(12) United States Patent
De Nanteuil et al.

(10) Patent No.: US 6,686,348 B2
(45) Date of Patent: Feb. 3, 2004

(54) METALLOPROTEASE INHIBITORS

(75) Inventors: Guillaume De Nanteuil, Suresnes (FR); Alain Benoist, Franconville (FR); Philippe Pastoureau, Sevres (FR); Massimo Sabatini, Garches (FR); John Hickman, Puteaux (FR); Alain Pierre, Les Alluets le Roi (FR); Gordon Tucker, Paris (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 123 days.

(21) Appl. No.: 10/036,689

(22) Filed: Dec. 21, 2001

(65) Prior Publication Data

US 2002/0137744 A1 Sep. 26, 2002

(30) Foreign Application Priority Data

Dec. 22, 2000 (FR) .............................. 00 16826

(51) Int. Cl.[7] .................. A61K 31/33; C07D 315/00; C07D 307/78; C07D 307/87; C07D 493/00
(52) U.S. Cl. .................. 514/183; 514/461; 514/469; 514/227.5; 514/337; 514/451; 549/200; 549/356; 549/435; 549/425; 549/426; 549/427; 549/456; 549/462; 549/469; 549/471; 549/497; 544/59; 544/60
(58) Field of Search .................. 514/461, 183, 514/469, 227.5, 337, 451; 549/200, 456, 462, 469, 471, 497, 356, 435, 425, 426, 427, 326; 544/59, 60

(56) References Cited

U.S. PATENT DOCUMENTS 5,866,587 A * 2/1999 de Nanteuil et al. ........ 514/302

FOREIGN PATENT DOCUMENTS

JP        80154    *  6/1983
JP       8157463   *  6/1996

OTHER PUBLICATIONS

Chemical Abstract DN 99: 175589, also cited as EP 80154.*

Chemical Abstract DN 125:208570, also cited as JP 08157463.*

* cited by examiner

Primary Examiner—Mukund J. Shah
Assistant Examiner—Sudhaker B. Patel
(74) Attorney, Agent, or Firm—The Firm of Hueschen and Sage

(57) ABSTRACT

A compound of formula (I):

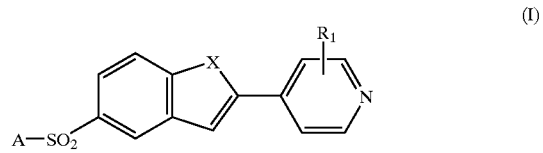

wherein:

$R_1$ represents hydrogen, halogen, alkyl or alkoxy,

X represents oxygen, sulphur or NR wherein R represents hydrogen or alkyl,

A represents any one of the groups described in the description, their isomers and addition salts thereof with a pharmaceutically acceptable acid or base and medicinal products containing the same are useful as metalloprotease inhibitor.

10 Claims, No Drawings

METALLOPROTEASE INHIBITORS

BACKGROUND OF THE INVENTION

The present invention relates to new metalloprotease inhibitors, to pharmaceutical compositions containing them.

In the physiological state, the synthesis of connective tissues is in dynamic equilibrium with the degradation of the extracellular matrix. That degradation is due to zinc proteases (metalloproteases) secreted by the cells of the existing matrix: they are, without implying any limitation, collagenases (MMP-1, MMP-8, MMP-13), gelatinases or collagenases of type TV (MMP-2, MMP-9) and stromelysins (MMP-3).

In the normal state, those catabolic enzymes are regulated in terms of their synthesis and their secretion, and in terms of their extracellular enzymatic activity, by natural inhibitors, such as $\alpha_2$-macroglobulin or the TIMPs (Tissue Inhibitors of MetalloProteinases), which form inactive complexes with the metalloproteases.

A common factor in pathologies in which those enzymes are implicated is an imbalance between the activity of the activated enzymes and that of their natural inhibitors, the consequence of which is excessive tissue degradation.

Uncontrolled and accelerated membrane degradation by resorption of the extracellular matrix catalysed by the metalloproteases is a parameter common to a number of pathological conditions, such as rheumatoid arthritis, arthrosis, tumour invasion and growth, including malignant spread and the formation of metastases, ulcerations, atherosclerosis, etc.

BB94, a metalloprotease inhibitor, has recently exhibited anti-tumour activity in clinical use, where it has proved to be active against ovarian cancers (Becket et al., DDT 1996, 1 (1), 16).

It may therefore be expected that a metalloprotease inhibitor will restore the equilibrium between protease and inhibitor and thus favourably modify the development of such pathologies.

DESCRIPTION OF THE PRIOR ART

A certain number of metalloprotease inhibitors have been described in the literature. There should be mentioned, more especially, the compounds described in Patent Specifications WO 95/35275, WO 95/35276, EP 606 046, WO 96/00214, EP 803 505, WO 97/20824 and EP 780 386.

The compounds of the present invention are not only new but have also proved to be more powerful metalloprotease inhibitors than those described in the literature, thus making them potentially useful in the treatment of cancer, rheumatic diseases, such as arthrosis and rheumatoid arthritis, atherosclerosis, etc.

DETAILED DESCRIPTION OF THE INVENTION

More specifically, the present invention relates to compounds of formula (I):

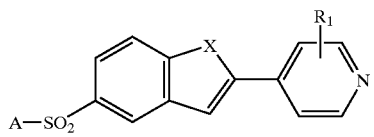

wherein:

$R_1$ represents a hydrogen atom, a halogen atom, a linear or branched $(C_1-C_6)$alkyl group or a linear or branched $(C_1-C_6)$alkoxy group, X represents an oxygen atom, a sulphur atom or an NR group wherein R represents a hydrogen atom or a linear or branched $(C_1-C_6)$alkyl group, A represents any one of the following groups:

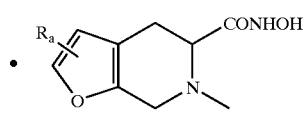

wherein $R_a$ represents a hydrogen atom, a halogen atom, a linear or branched $(C_1-C_6)$-alkyl group or a linear or branched $(C_1-C_6)$alkoxy group,

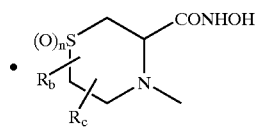

wherein $R_b$ and $R_c$, which may be identical or different, represent a hydrogen atom or a linear or branched $(C_1-C_6)$alkyl group, and n is 0, 1 or 2, or

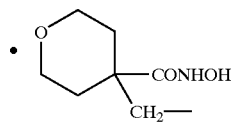

their isomers, N-oxides, and addition salts thereof with a pharmaceutically acceptable acid or base.

Among the pharmaceutically acceptable acids there may be mentioned by way of non-limiting example hydrochloric acid, hydrobromic acid, sulphuric acid, phosphonic acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid, etc.

Among the pharmaceutically acceptable bases there may be mentioned by way of non-limiting example sodium hydroxide, potassium hydroxide, lithium hydroxide, triethylamine, tert-butylamine, etc.

The preferred compounds of the invention are the compounds of formula (I) wherein X represents an oxygen atom.

$R_1$ is preferably a hydrogen atom.

When A represents a group

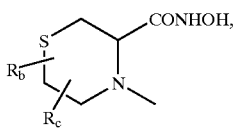

that group is preferably the group

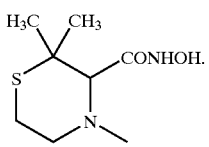

The preferred compounds of the invention are:
N-hydroxy-(5R)-6-{[2-(4-pyridyl)-1-benzofuran-5-yl]sulphonyl}-4,5,6,7-tetrahydro-furo[2,3-c]pyridine-5-carboxamide,
N-hydroxy-(3S)-2,2-dimethyl-4-{[2-(4-pyridyl)-1-benzofuran-5-yl]sulphonyl}-3-thiomorpholinecarboxamide,
N-hydroxy-4-{{[2-(4-pyridyl)-1-benzofuran-5-yl]sulphonyl}methyl}tetrahydro-2H-pyran-4-carboxamide,
and addition salts thereof.

The invention relates also to a process for the preparation of compounds of formula (I).

When the compounds of formula (I) are those wherein A represents any one of the groups:

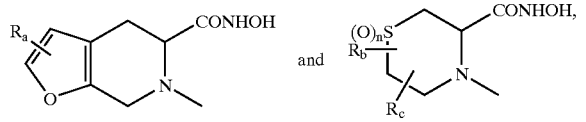

the process is characterised in that there is used as starting material a compound of formula (II):

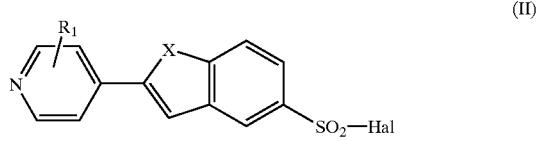

wherein $R_1$ and X are as defined for formula (I) and Hal represents a halogen atom, which is reacted with any one of the compounds (IIIa) and (IIIb), in racemic form or in the form of a specific isomer:

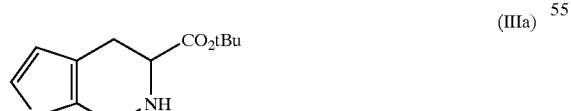

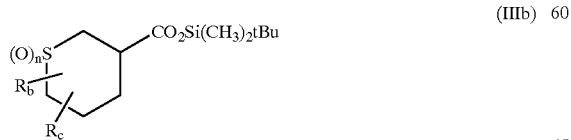

wherein Rb, Rc and n are as defined for formula (I), to yield the compounds of formulae (IVa) and (IVb), respectively:

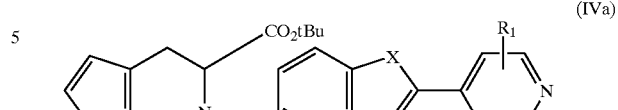

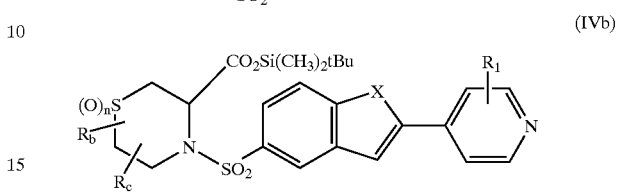

wherein X, $R_1$, Rb, Rc and n are as defined for formula (I), which are deprotected to yield the compounds of formulae (Va) and (Vb), respectively,

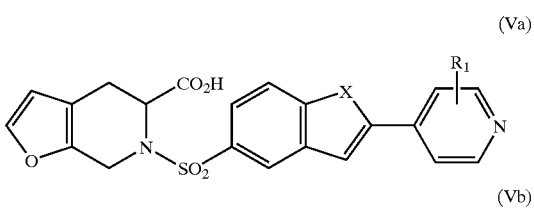

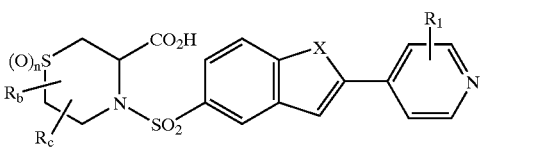

wherein X, $R_1$, Rb, Rc and n are as defined for formula (I), which are subjected to the action of an O-substituted hydroxylamine, to yield, after deprotection of the hydroxamate function, the compounds of formulae (I/a) and (I/b), respectively:

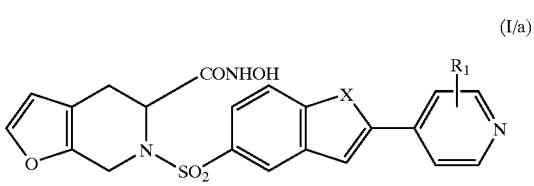

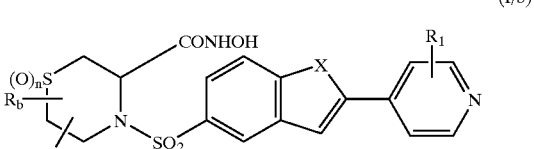

wherein X, $R_1$, Rb, Rc and n are as defined for formula (I), which compounds of formulae (I/a) and (I/b):
  are optionally converted to the corresponding N-oxides,
  are purified, if necessary, in accordance with a conventional purification technique,
  are separated, where appropriate, into their isomers in accordance with a conventional separation technique, and
  converted, if desired, into addition salts thereof with a pharmaceutically acceptable acid or base.

When the compounds of formula (I) are those wherein A represents the group:

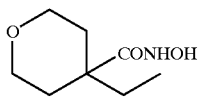

the process is characterised in that there is used as starting material a compound of formula (VI):

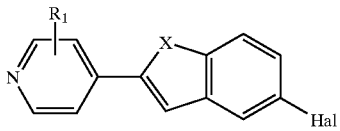
(VI)

wherein $R_1$ and X are as defined for formula (I), and Hal represents a halogen atom,
which is reacted with a compound of formula (VII):

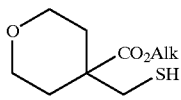
(VII)

wherein Alk represents a linear or branched $(C_1-C_6)$alkyl group, to yield, after acid hydrolysis, the compound of formula (VIII):

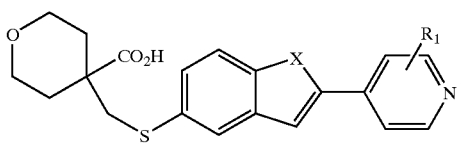
(VIII)

wherein $R_1$ and X are as defined for formula (1),
which is reacted with an oxidation reagent, to yield the compound of formula (IX):

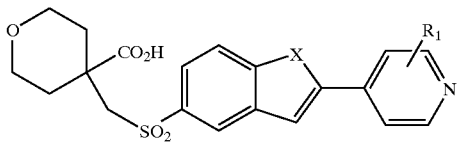
(IX)

wherein X and $R_1$ are as defined for formula (I), which is subjected to the action of an O-substituted hydroxylamine, to yield, after deprotection of the hydroxamate function, the compound of formula (I/c), a particular case of the compounds of formula (I):

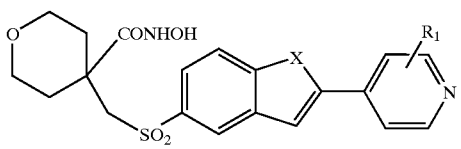
(I/c)

wherein $R_1$ and X are as defined for formula (I), which is optionally converted to the corresponding N-oxide, which is purified, if necessary, in accordance with a conventional purification technique, separated, where appropriate, into its isomers in accordance with a conventional separation technique, and converted, if desired, into addition salts thereof with a pharmaceutically acceptable acid or base.

The compounds of formulae (II) and (VI) are obtained using as starting material a compound of formula (X):

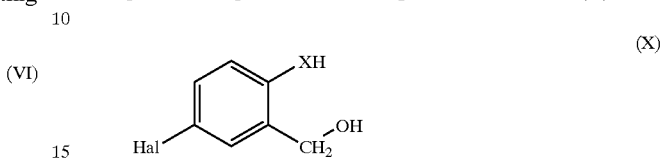
(X)

wherein Hal represents a halogen atom and X is as defined for formula (I),
which is reacted with triphenylphosphine bromide to yield the compound of formula (XI):

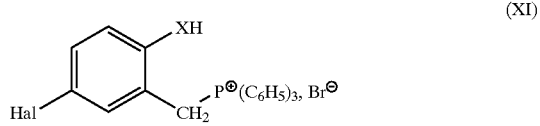
(XI)

wherein Hal and X are as defined hereinbefore,
which is reacted with an isonicotinoyl chloride of formula (XII):

(XII)

wherein $R_1$ is as defined for formula (I),
to yield a compound of formula (VI):

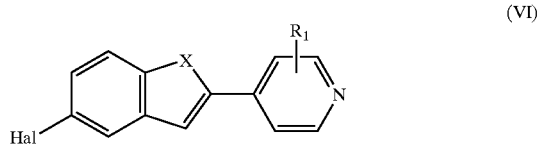
(VI)

wherein Hal, X and $R_1$ are as defined hereinbefore,
which is then converted to the compound of formula (XIII) in the presence of sulphur dioxide and of n-butyllithium:

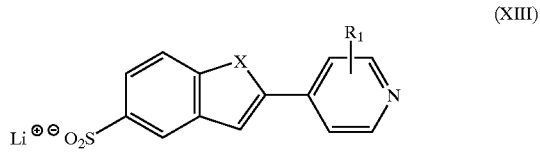
(XIII)

wherein $R_1$ and X are as defined hereinbefore,
and then to the compound of formula (II) in the presence of sulphuryl halide:

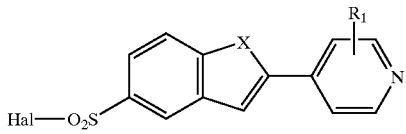

(II)

wherein Hal, X and R₁ are as defined hereinbefore.

The invention relates also to pharmaceutical compositions comprising as active ingredient at least one compound of formula (I) with one or more appropriate inert non-toxic excipients. Among the pharmaceutical compositions according to the invention there may be mentioned more especially those that are suitable for oral, parenteral (intravenous or sub-cutaneous) or nasal administration, tablets or dragees, sublingual tablets, gelatin capsules, lozenges, suppositories, creams, ointments, dermal gels, injectable preparations, drinkable suspensions, etc.

The useful dosage can be adapted according to the nature and severity of the disorder, the route of administration and the age and weight of the patient. The dosage ranges from 0.01 to 2 g per day in one or more administrations.

The following Examples illustrate the invention but do not limit it in any way.

The starting materials used are known products or are prepared according to known procedures.

The preparations yield synthesis intermediates for use in the preparation of the compounds of the invention.

The structures of the compounds described in the Examples and Preparations were determined in accordance with the usual spectrophotometric techniques (infrared, NMR, mass spectrometry, etc.).

Preparation A: Ethyl 4-(sulphanylmethyl)tetrahydro-2H-pyran-4-carboxylate

Step A: Ethyl 4-[(acetylsulphanyl)methyl]tetrahydro-2H-pyran-4-carboxylate

Under argon, 47 g of triphenylphosphine are dissolved in 350 ml of tetrahydrofuran (THF). After cooling to 0° C., 34.9 ml of diisopropyl azodicarboxylate (DIAD) are added to that solution. After 30 minutes' stirring, a solution containing 89 mmol of ethyl 4-(hydroxymethyl) tetrahydro-2H-pyran-4-carboxylate and 12.8 ml of thioacetic acid in 300 ml of THF is added.

After stirring overnight at room temperature, and evaporation to dryness, the residue is taken up in ether. After filtration, the filtrate is evaporated and yields the expected product in the form of an oil, which is purified by chromatography over a silica column using a mixture of dichloromethane/ethyl acetate (90/10) as eluant.

Step B: Ethyl 4-(sulphanylmethyl)tetrahydro-2H-pyran-4-carboxylate 92 ml of a 2.2N hydrochloric acid solution in ethanol are added to 67.4 mmol of the compound obtained in the preceding Step dissolved in 50 ml of ethanol. After stirring overnight, the whole is evaporated to dryness to yield the expected product in the form of an oil.

Preparation B: 5Bromo-2-(4-pyridyl)benzofuran

Step A (5-Bromo-2-hydroxybenzyl)triphenylphosphonium Bromide 169 g of triphenylphosphine bromide are added to 490 mmol of 4-bromo-2-(hydroxymethyl)phenol suspended in 500 ml of acetonitrile. The whole is heated at 100° C. for 2 hours. After cooling, the precipitate that has formed is filtered off and dried to yield the expected product.

Melting point: 260° C.

Step B: 5-Bromo-2-(4-Pyridyl)benzofuran 256 ml of triethylamine are added to 243 g of the product obtained in the preceding Step in 2 liters of toluene in the presence of 90.1 g of isonicotinoyl chloride. The whole is heated at 100° C. for 24 hours. After cooling, the precipitate that has formed is filtered off and yields the expected product after recrystallisation from ethyl acetate.

Melting point: 160° C.

Preparation C: 2-(4-Pyridyl)-)1-benzofuran-5-sulphonyl Chloride

Step A: {[2-(4-Pyridyl)-1-benzofuran-5-yl]sulphonyl}lithium n-Butyllithium is added, at −72° C., to 60.2 mmol of the compound obtained in Preparation B suspended in tetrahydrofuran. After 90 minutes at −72° C., a stream of SO₂ is passed through the mixture for 1 hour. After 2 days at room temperature, the solid that has formed is filtered off and rinsed with ether to yield the expected product.

Step B:2-(4-Pyridyl)-1-benzofuran-5-sulphonyl Chloride 59 mmol of the product obtained in the preceding Step are suspended in 80 ml of dichloromethane. After cooling to 0° C., 5.7 ml of sulphuryl chloride are added dropwise. After a night at room temperature, the precipitate that has formed is filtered off and rinsed with ether to yield the expected product.

Melting point: 210° C.

EXAMPLE 1

N-Hydroxy-(5R)-6-{[2-(4-pyridyl)-1-benzofuran-5-yl]sulphonyl}-4,5,6,7,-tetrahydrofuro[2,3-c]pyridine-5-carboxamide hydrochloride Step A: (5R)-6-{[(4-Pyridyl)-1-benzofuran-5-yl]sulphonyl}-4,5,6,7-tetra-hydrofuro[2,3-c]pyridine-5-carboxylic acid tert-butyl Ester 30 mmol of (5R)-4,5,6,7-tetrahydrofuro[2,3-c]pyridine-5-carboxylic acid tert-butyl ester hydrochloride are placed in 150 ml of pyridine. 30 mmol of 2-(4-pyridyl)-1-benzofuran-5-sulphonyl chloride described in Preparation C are then added at room temperature and the whole is heated at 60° C. overnight.

After removal of the pyridine by evaporation, taking up of the residue in dichloromethane, washing with water, drying and evaporation, the expected product is obtained in the form of an oil, which is purified by chromatography over silica using a mixture of dichloromethane/ethanol (98/2) as eluant.

Step B: (5R)-6-{[2-(4-Pyridyl)-1-(benzofuran-5-yl]sulphonyl}4,5,6,7-tetrahydrofuro[2,3-c]pyridine-5-carboxylic Acid 2.4 ml of anisole are added to 22 mmol of the ester obtained in the preceding Step dissolved in 250 ml of dichloromethane. The whole is cooled to 0° C. and 17 ml of trifluoroacetic acid are added. The whole is maintained at room temperature overnight. After evaporation to dryness, the residue is purified by chromatography over silica using a mixture of dichloromethane/methanol (85/15) as eluant to yield the expected product.

Step C: N-Allyloxy-(5R)-6-{[2-(4-pyridyl)-1-benzofuran-5-yl]sulphonyl}-4,5,6,7-tetrahydrofuro[2,3-c]pyridine-5-carboxamide To a solution, cooled to 0° C., containing 12 mmol of the acid obtained in the preceding Step in 150 ml of dichloromethane, there are added 10.3 ml of diisopropylethylamine, 1.65 g of 1-hydroxybenzotriazole, a solution containing 1.6 g of O-allylhydroxylamine hydrochloride in 50 ml of dimethylformamide, and 4.65 g of O-benzotriazolyl-tetramethylisouronium tetrafluoroborate (TBTU). The whole is maintained at room temperature overnight. After evaporation to dryness, the residue is taken up in dichloromethane. After washing with water, drying and evaporation, a residue is obtained which yields the expected product after purification over a silica column using a mixture of dichloromethane/ethanol/ammonia (98/2/0.2) as eluant.

Step D: N-Hydroxy-(5R)-6-{[2-(4-pyridyl)-1-benzofuran-5-yl]sulphonyl}-4,5,6,7-tetrahydrofuro[2,3-c]pyridine-5-carboxamide Hydrochloride 300 mg of the Pd catalyst $(PPh_3)_2Cl_2$ and 1.5 ml of acetic acid are added to 8.55 mmol of the product obtained in the preceding Step in 150 ml of dichloromethane. After 5 minutes, 4.9 ml of tributyltin hydride are added. The whole is maintained at room temperature for 30 minutes and then evaporated. After the residue has been taken up in acetonitrile, 20 ml of 1N hydrochloric acid are added and the whole is diluted with water. The aqueous phase is washed with ether and then lyophilised to yield the expected product.

Elemental microanalysis:

|  | C % | H % | N % | Cl % | S % |
|---|---|---|---|---|---|
| calculated | 53.00 | 3.81 | 8.83 | 7.45 | 6.74 |
| found | 52.94 | 3.81 | 8.70 | 7.30 | 6.65 |

EXAMPLE 2

N-Hydroxy-(3S)-2,2-dimethyl-4-{[2-(4-pyridyl)-benzofuran-5-yl]sulphonyl}-3-thiomorpholinecarboxamide Step A: 4-{[2-(4-Aminophenyl)-1-benzofuran-5-yl]sulphonyl}-2,2-dimethyl-3-thiomorpholinecarboxylic acid tert-butyl(dimethyl)silyl Ester 58.7 mmol of 2,2-dimethyl-3-thiomorpholinecarboxylic acid tert-butyl(dimethyl)silyl ester are dissolved in 500 ml of anhydrous dichloromethane. At −20° C., there are added 16 ml of N-methylmorpholine, followed by 57.5 mmol of 2-(4-pyridyl)-1-benzofuran-5-sulphonyl chloride described in Preparation C. The whole is stirred for 48 hours at room temperature and then poured into 300 ml of water. After decanting, washing with water, drying and evaporation, the expected product is obtained in the form of an oil.

Step B: 4-{[2-(4-Aminophenyl)-1-benzofuran-5-yl}-2,2-dimethyl-3-thiomorpholinecarboxylic Acid 33 g of the compound obtained in the preceding Step are dissolved in 400 ml of anhydrous methanol. The whole is refluxed for 2 hours and then evaporated. The expected product is obtained by crystallisation of the residue from ether.

Step C: N-(Allyloxy)-4-{[2-(4-aminophenyl)-1-benzofuran-5-yl]sulphonyl}-2,2-dimethyl-3-thiomorpholinecarboxamide The expected product is obtained according to the process described in Step C of Example 1 starting from the product described in the preceding Step.

Step D: N-Hydroxy-(3S)-2,2-dimethyl-4-{[2-(4-pyridyl)-1-benzofuran-5-yl]-sulphonyl}-3-thiomorpholinecarboxamide To 10.2 mmol of the compound described in the preceding Step dissolved in 70 ml of dichloromethane, there are added 360 mg of the Pd catalyst $(PPh_3)_2Cl_2$ and 1.75 ml of acetic acid, followed 5 minutes later by 5.8 ml of tributyltin hydride. After 20 minutes' stirring, 70 ml of ether are added. The insoluble matter is filtered off and washed with ether, taken up in a mixture of acetonitrile/water (50/50) and, after lyophilisation, yields the expected product.

Elemental microanalysis:

|  | C % | H % | N % | S % |
|---|---|---|---|---|
| calculated | 53.68 | 4.73 | 9.39 | 14.33 |
| found | 53.38 | 4.81 | 9.08 | 13.91 |

EXAMPLE 3

N-Hydroxy-4-{{[2-(4-pyridyl)-1-benzofuran-5-yl]sulphonyl}-methyl}tetrahydro-2H-pyran-4-carboxamide Step A: 4-{{[2-(4-Pyridyl)-1-benzofuran-5-yl]sulphonyl}methyl}tetrahydro-2H-pyran-4-carboxylic Acid Ethyl Ester 23.9 mmol of 5-bromo-2-(4-pyridyl)benzofuran described in Preparation B, 7.32 g of the compound described in Preparation A, 431 mg of tris-(dibenzylideneacetone)dipalladium and 1.05 g of 1,1'-bis(diphenyl)phosphinoferrocene are placed in 75 ml of N-methyl-pyrrolidone. The whole is heated at 100° C. for 48 hours. After evaporation, the residue is taken up in ethyl acetate and a saturated sodium chloride solution. After filtration, extraction with ethyl acetate and evaporation, the residue is purified by chromatography over a silica column using a mixture of dichloromethane/ethyl acetate (9/1) as eluant. The expected product then crystallises out.

Melting point: 92° C.

Step B: 4-{{[2-(4-Pyridyl)-1-benzofuran-5-yl]sulphanyl}methyl}tetrahydro-2H-pyran-4-carboxylic Acid 7.5 g of the ester obtained in the preceding Step are placed in 200 ml of 6N hydrochloric acid. The whole is refluxed overnight. After cooling, the pH of the solution is adjusted to 7 by the addition of sodium hydroxide. The precipitate that forms is filtered off and washed with water to yield the expected product.

Melting point: 227° C.

Step C: 4-{{[2-(4-Pyridyl)-1-benzofuran-5-yl]sulphonyl}methyl}tetrahydro-2H-pyran-4-carboxylic Acid 18 mmol of the compound obtained in the preceding Step are placed in 116 ml of water and 140 ml of acetonitrile. The whole is cooled in an ice-bath and 17.65 g of Oxone are added in portions. The mixture is left at room temperature for 48 hours. After evaporation, the pH is adjusted to 7 and the expected product precipitates.

Melting point: 217° C.

Step D: 4-{{[2-(4-Pyridyl)-1-benzofuran-5-yl]sulphonyl}methyl}-N-(allyloxy)-tetrahydro-2H-pyran-4-carboxamide The expected product is obtained in accordance with the process described in Step C of Example 1 starting from the compound described in the preceding Step.

Step E: N-Hydroxy-4-{{[2-(4-pyridyl)-1-benzofuran-5-yl]sulphonyl}-methyl}tetrahydro-2H-pyran-4-carboxamide The expected product is obtained in accordance with the process described in Step D of Example 1 starting from the compound described in the preceding Step.

| Elemental microanalysis: | | | | |
|---|---|---|---|---|
| | C % | H % | N % | S % |
| calculated | 57.68 | 4.84 | 6.73 | 7.70 |
| found | 57.71 | 4.90 | 6.19 | 7.23 |

EXAMPLE 4

N-Hydroxy-(3S)-2,2-dimethyl-4-{[2-(4-pyridyl)-1-benzofuran-5-yl]sulphonyl}-3-thiomorpholinecarboxamide 1-oxide The expected product is obtained in accordance with the process described in Example 2, in Step A replacing 2,2-dimethyl-3-thiomorpholinecarboxylic acid by 2,2-dimethyl-3-thiomorpholinecarboxylic acid 1-oxide.

EXAMPLE 5

N-Hydroxy-(3S)-2,2-dimethyl-4-{[2-(4-pyridyl)-1-benzofuran-5-yl]sulphonyl}-3-thiomorpholinecarboxamide 1,1-dioxide The expected product is obtained in accordance with the process described in Example 2, in Step A replacing 2,2-dimethyl-3-thiomorpholinecarboxylic acid by 2,2-dimethyl-3-thiomorpholinecarboxylic acid 1,1-dioxide.

EXAMPLE 6

N-Hydroxy-(3S)-2,2-dimethyl-4-{[2-(4-pyridyl oxide)-1-benzofuran-5-yl]sulphonyl}-3-thiomorpholinecarboxamide The expected product is obtained by oxidation of the compound described in Example 2.

Pharmacological Study of the Compounds of the Invention

EXAMPLE A

Enzymatic Inhibition of Metalloproteases

Six recombinant human enzymes, MMP-1 (interstitial collagenase), MMP-2 (gelatinase A), MMP-3 (stromelysin 1), MMP-8 (neutrophil collagenase), MMP-9 (gelatinase B) and MMP-13 (collagenase 3) are activated with APMA (4-aminophenylmercuric acetate). The enzymatic tests on MMP-1, -2, -8, -9 and -13 are carried out using the following peptidomimetic substrate:

DnpProGhaGlyCys(Me)HisAlaLys(Nma)NH$_2$, which is cleaved between the glycine and the cysteine to yield a fluorescent product described by D. M. BICKETT et al. (Anal. Biochem., 212, 58–64, 1993). The enzymatic test on MMP-3 is carried out using the following peptidomimetic substrate:

McaArgProLysProTyrAlaNvaTrpMetLys(Dnp)NH$_2$, which is cleaved between alanine and norvaline to yield a fluorescent product described by H. NAGASE et al. (J. Biol. Chem., 269, 20952–20957, 1994).

The reactions, carried out in a buffer of 50 mM Tris, 200 mM NaCl, 5 mM CaCl$_2$, 0.1% Brij 35 at pH 7.7, are initiated using 20 µM substrate in a total volume of 100 µl at 37° C. The fluorescence obtained after six hours is read in a 96-well plate in a fluorimeter equipped with a combination of 360 nm and 460 nm filters for excitation and emission. The compounds of the invention have IC$_{50}$ values of from $10^{-10}$ to $10^{-8}$M for all of the MMPs with the exception of MMP-1. The collagenases MMP-13 and MMP-8 exhibit a specificity of a factor of 1000 compared with collagenase MMP-1.

EXAMPLE B

In Vitro Degradation of the Cartilage Matrix

The compounds of the invention were studied in a model of damage to the cartilage matrix induced by IL-1β. The tests, carried out on rabbit cartilage, relate:

on the one hand, to the degradation of collagen: calorimetric assay, according to the technique of Grant (GRANT R. A. Estimation of OH-proline by the autoanalyser, J. Clin. Path., 17, 685, 1964), of the OH-proline fraction released by the tissue in contact with IL-1β (10 ng/ml) and plasmin (0.1 U/ml) for 2 days;

on the other hand, to the degradation of proteoglycans: radio-isotopic measurement of the fraction of glycosaminoglycans released after 24 hours' stimulation with IL-1β (10 ng/ml) by the tissue pre-labelled with $^{35}SO_4$, over the course of 24 hours in contact with APMA ($5 \times 10^{-4}$M).

The compounds of the invention were studied by addition to the culture medium for the 3 days of the test. For concentrations of from $10^{-9}$ to $10^{-6}$M, they strongly inhibited the degradation of collagen and of proteoglycans.

EXAMPLE C

In Vitro Angiogenesis

Portions of thoracic aorta of male Fischer 344 rats aged from 8 to 12 weeks are immersed in a type I collagen gel according to the method of Nicosia and Ottinetti (Lab. Invest., 63, 115, 1990). After five days of culture in a medium without serum, the preparations are examined under a microscope and the formation of pseudo-vessels is quantified in terms of vascular density after digitisation and image analysis. At concentrations of from $10^{-9}$ to $10^{-6}$M, the compounds of the invention selectively block the formation of pseudo-vessels from endothelial cells, without affecting fibroblastic cells.

EXAMPLE D

Pharmaceutical Composition

Formulation for the preparation of 1000 tablets each containing a dose of 100 mg of active ingredient

| | |
|---|---|
| Compound of Example 1 | 100 g |
| Hydroxypropylcellulose | 2 g |
| Wheat starch | 10 g |
| Lactose | 100 g |
| Magnesium stearate | 3 g |
| Talc | 3 g |

What is claimed is:

1. A compound of formula (I):

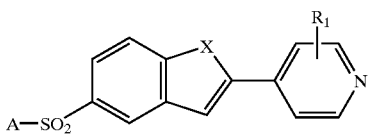

wherein:

R$_1$ represents hydrogen, halogen, linear or branched (C$_1$–C$_6$)alkyl or line or branched (C$_1$–C$_6$)alkoxy, X represents oxygen wherein R represents hydrogen or linear or branched (C$_1$–C$_6$)alkyl and, A is selected from the following groups:

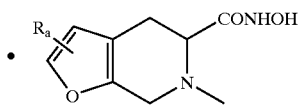

wherein R$_a$ is selected from hydrogen, halogen, linear or branched (C$_1$–C$_6$)-alkyl and linear or branched (C$_1$–C$_6$) alkoxy,

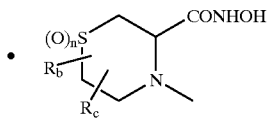

wherein R$_b$ and R$_c$, which may be identical or different, represent hydrogen or linear or branched (C$_1$–C$_6$)alkyl, and n is 0, 1 or 2, and

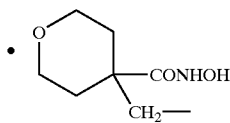

its isomers, N-oxides, and addition salts thereof with a pharmaceutically acceptable acid or base.

2. A compound of claim 1, wherein A represents the group:

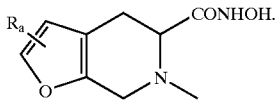

3. A compound of claim 1, wherein A represents the group:

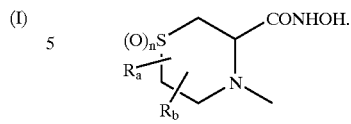

4. A compound of claim 1, wherein A represents the group:

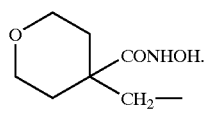

5. A compound of claim 3, wherein A represents the group:

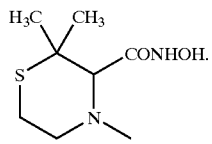

6. The compound of claim 1 which is N-hydroxy-(5R)-6-{[2-(4-pyridyl)-1-benzofuran-5-yl]sulphonyl}-4,5,6,7-tetrahydro[2,3-c]-pyridine-5-carboxamide.

7. The compound of claim 1, which is N-hydroxy-(3S)-2,2-dimethyl-4-{[2-(4-pyridyl)-1-benzofuran-5-yl]sulphonyl}-3-thiomor-pholine-carboxamide.

8. The compound of claim 1 which is N hydroxy-4-{{[2-(4-pyridyl)-1-benzofuran-5-yl]sulphonyl}methyl}tetrahydro-2H-pyran-4-carboxamide.

9. A method for treating an animal or human living body afflicted with a condition requiring a metalloprotease inhibitor comprising the step of administering to the living body an amount of a compound of claim 1 which is therapeutically effective for alleviation of said condition.

10. A pharmaceutical composition useful in treating an animal or human living body afflicted with a condition requiring a metalloprotease inhibitor comprising as active principle a therapeutically effective amount of a compound as claimed in claim 1, together with one or more pharmaceutical acceptable excipients or vehicles.

* * * * *